US010429326B2

United States Patent
Hoffman et al.

(10) Patent No.: US 10,429,326 B2
(45) Date of Patent: Oct. 1, 2019

(54) X-RAY OPTICS ASSEMBLY WITH SWITCHING SYSTEM FOR THREE BEAM PATHS, AND ASSOCIATED X-RAY DIFFRACTOMETER

(71) Applicant: Bruker AXS GmbH, Karlsruhe (DE)

(72) Inventors: Frank Hans Hoffman, Maximiliansau (DE); Kai Uwe Mettendorf, Karlsruhe (DE)

(*) Notice: Subject to any disclaimer, the term of this patent is extended or adjusted under 35 U.S.C. 154(b) by 296 days.

(21) Appl. No.: 15/370,047

(22) Filed: Dec. 6, 2016

(65) Prior Publication Data

US 2017/0176356 A1 Jun. 22, 2017

(30) Foreign Application Priority Data

Dec. 18, 2015 (DE) .......... 10 2015 226 101

(51) Int. Cl.
*G01N 23/207* (2018.01)
*G21K 1/06* (2006.01)

(52) U.S. Cl.
CPC ............ *G01N 23/207* (2013.01); *G21K 1/06* (2013.01); *G01N 2223/315* (2013.01); *G21K 2201/061* (2013.01); *G21K 2201/062* (2013.01)

(58) Field of Classification Search
CPC .. G01N 2223/315; G01N 23/207; G21K 1/06; G21K 2201/061
See application file for complete search history.

(56) References Cited

U.S. PATENT DOCUMENTS 4,462,689 A * 7/1984 Kabler ............... G21K 1/06
250/372
4,481,653 A * 11/1984 Tatchyn ............. G21K 1/06
378/85

(Continued)

FOREIGN PATENT DOCUMENTS

DE 19962503 A1 8/2000
DE 102009047672 A1 6/2011
(Continued)

OTHER PUBLICATIONS

Fujii et. al. "A Compact Ultrahigh Vacuum X-Ray Diffractometer for Surface Glancing Scattering Using a Rotating-Anode Source", Rev. Sci. Instrum. 68 (5), May 1997.

(Continued)

*Primary Examiner* — Dani Fox
*Assistant Examiner* — Soorena Kefayati
(74) *Attorney, Agent, or Firm* — Benoit & Cote, Inc.

(57) ABSTRACT

An X-ray optics assembly for an X-ray diffractometer is provided, comprising a multilayer mirror, in particular a Goebel mirror, and a switching system with which beam paths for an X-ray beam are selectable. The X-ray optics assembly includes a monochromator, in particular a channel-cut crystal, and three beam paths for the X-ray beam are selectable using the switching system. A first beam path in a first position of the switching system leads past the multilayer mirror and leads past the monochromator, a second beam path in a second position of the switching system contains the multilayer mirror and leads past the monochromator, and a third beam path in a third position of the switching system contains the multilayer mirror and contains the monochromator. The invention provides an X-ray optics assembly and an X-ray diffractometer which (Continued)

may be used even more universally for various measurement geometries in a simple manner.

24 Claims, 14 Drawing Sheets

(56) References Cited

U.S. PATENT DOCUMENTS

| | | | | |
|---|---|---|---|---|
| 4,726,047 | A * | 2/1988 | Brouwer | G01N 23/20008 378/73 |
| 5,475,728 | A | 12/1995 | Smith et al. | |
| 5,509,043 | A * | 4/1996 | Van Der Sluis | G21K 1/06 378/70 |
| 5,802,137 | A * | 9/1998 | Wilkins | A61B 6/484 250/363.1 |
| 6,226,349 | B1 * | 5/2001 | Schuster | G01N 23/20 378/81 |
| 6,240,159 | B1 * | 5/2001 | Kohno | G01N 23/207 378/45 |
| 6,359,964 | B1 * | 3/2002 | Kogan | G01N 23/20 378/70 |
| 6,504,900 | B2 * | 1/2003 | Kondo | G01N 23/20 378/34 |
| 6,665,372 | B2 * | 12/2003 | Bahr | G01N 23/20 378/71 |
| 6,807,251 | B2 * | 10/2004 | Okanda | G01N 23/20 378/71 |
| 8,085,900 | B2 * | 12/2011 | Omote | G01N 23/223 378/84 |
| 8,345,822 | B2 | 1/2013 | Ollinger | |
| 2001/0053198 | A1 * | 12/2001 | Kikuchi | G21K 1/06 378/84 |
| 2004/0042584 | A1 * | 3/2004 | Blank | G01N 23/20016 378/81 |
| 2004/0190681 | A1 * | 9/2004 | Omote | G01N 23/20 378/71 |
| 2006/0013362 | A1 * | 1/2006 | Omote | G01B 15/02 378/70 |
| 2007/0003013 | A1 * | 1/2007 | Matsuo | G01N 23/00 378/84 |
| 2009/0225946 | A1 * | 9/2009 | Inaba | G01N 23/20 378/73 |
| 2011/0135059 | A1 * | 6/2011 | Ollinger | G21K 1/06 378/84 |
| 2013/0114157 | A1 * | 5/2013 | Deyhim | G02B 7/182 359/872 |
| 2013/0287178 | A1 * | 10/2013 | Ryan | G21K 1/06 378/145 |
| 2015/0098547 | A1 * | 4/2015 | Wakasaya | G01N 23/083 378/51 |
| 2015/0293041 | A1 * | 10/2015 | Mukaide | G01N 23/207 378/64 |
| 2017/0146468 | A1 * | 5/2017 | Mukaide | G01N 23/207 |

FOREIGN PATENT DOCUMENTS

| | | |
|---|---|---|
| EP | 1324023 A2 | 7/2003 |
| EP | 1912061 A1 | 4/2008 |
| JP | 09049811 A1 | 2/1997 |
| JP | 2013221874 A1 | 10/2013 |
| WO | 03091716 A1 | 11/2003 |

OTHER PUBLICATIONS

Shu D. et al. "Precision Mechanical Design of an UHV-Compatible Artificial Channel-Cut X-ray Monochromator", Proc. of SPIE vol. 66500 (2007).

* cited by examiner

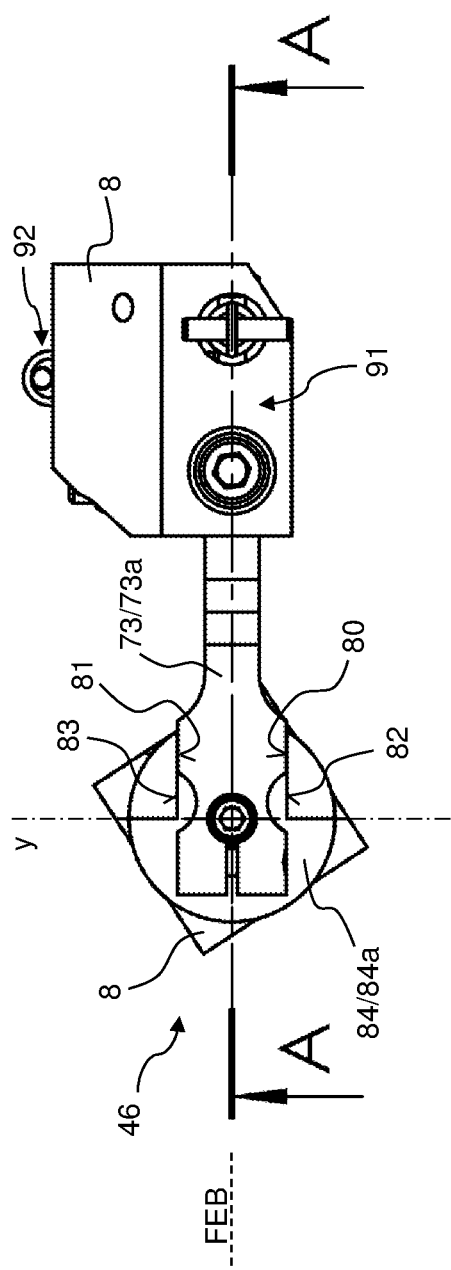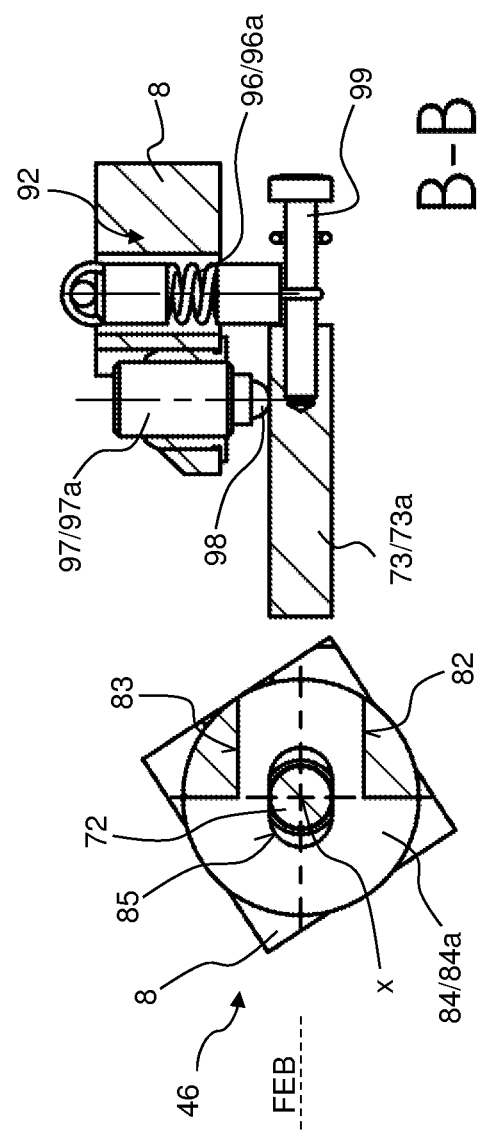

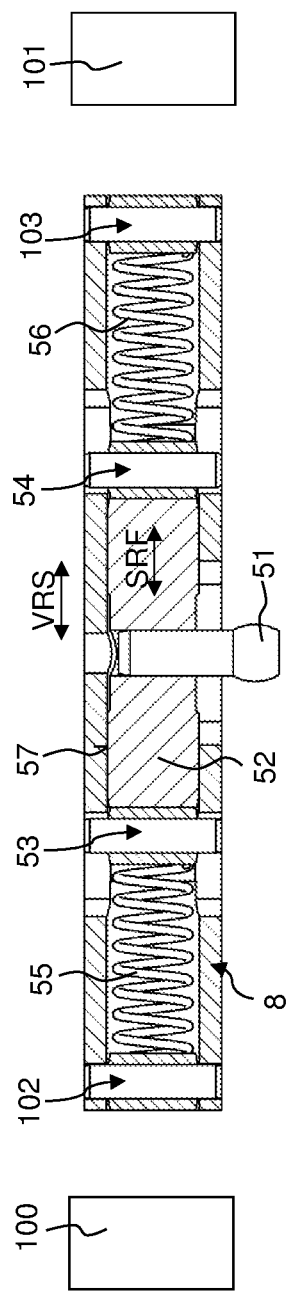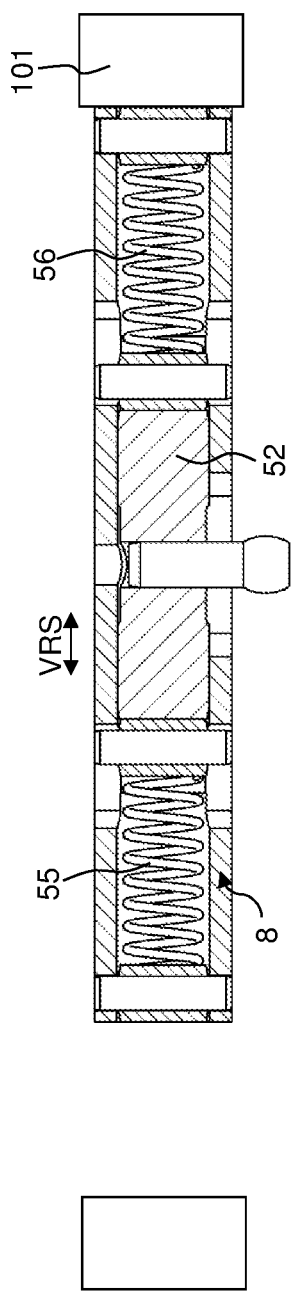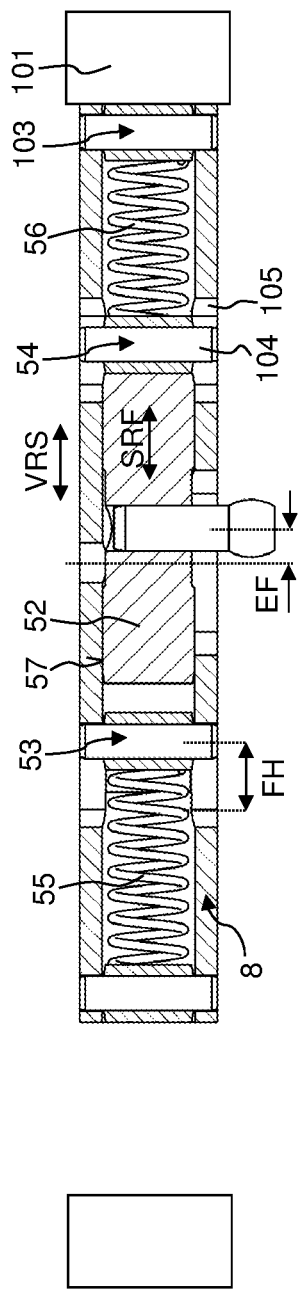

X-RAY OPTICS ASSEMBLY WITH SWITCHING SYSTEM FOR THREE BEAM PATHS, AND ASSOCIATED X-RAY DIFFRACTOMETER

BACKGROUND OF THE INVENTION

Field of the Invention

The invention relates to an X-ray optics assembly for an X-ray diffractometer, including a multilayer mirror, in particular a Goebel mirror, and a switching system with which beam paths for an X-ray beam are selectable. Such an X-ray optics assembly is known from DE 10 2009 047 672 A1, for example.

Description of the Related Art

X-ray diffraction (XRD) is a powerful method of instrumental analytics with which crystalline materials in particular may be characterized. Various measurement geometries are used, depending on the analytical task. For example, the Bragg-Brentano geometry, in which an X-ray beam, after reflection on the sample, is focused on the detector (or the detector aperture), is frequently used in powder diffraction. In the parallel beam geometry, an X-ray beam is directed in parallel onto the sample, for example for texture measurements. For the various measurement geometries, different X-ray optics elements are required in the beam path.

In practice, the same X-ray diffractometer is frequently used with different measurement geometries in alternation. Accordingly, it is desirable to minimize the modification and adjustment measures necessary for switching the measurement geometry.

DE 10 2009 047 672 A1 discloses an X-ray optics design in which a switch is made between a reflection geometry, with an X-ray mirror in the beam path on the primary beam side, and a transmission geometry with two X-ray mirrors in the beam path on the primary beam side, by means of a displaceable or rotatable aperture system. Modification and adjustment operations are thus minimized, or unnecessary.

An X-ray diffractometer is known from U.S. Pat. No. 6,807,251 B2 for measurements in a focusing geometry without reflection on a multilayer mirror, and in a parallel geometry with reflection on the multilayer mirror, whereby one of the beam paths may be selected using a rotatable slitted disk behind the multilayer mirror. In addition, a divergence slit is provided which may be moved between the beam paths.

The known X-ray diffractometers allow a switch between two beam paths, for example a Bragg-Brentano geometry and a parallel beam geometry. For many analytical tasks this is sufficient; in some cases, however, high-resolution X-ray diffraction information is necessary which is not available using the known switchable X-ray optics.

U.S. Pat. No. 6,359,964 B1 describes a device for X-ray analysis, having a parabolic multilayer mirror for parallelizing X-rays, and a device for monochromatizing the parallelized radiation, in particular using a two-crystal monochromator. The multilayer mirror may be rotated by 180°, as the result of which the X-ray beam is directed either via the multilayer mirror and the monochromator onto the object to be examined, or alternatively, directly from the multilayer mirror onto the object. High-resolution X-ray diffraction measurements are possible using the monochromatized X-ray beam.

SUMMARY OF THE INVENTION

The invention is directed to providing an X-ray optics assembly and an X-ray diffractometer which may be used even more universally for various measurement geometries in a simple manner. This is achieved by an X-ray optics assembly of the type mentioned at the outset, which is characterized in that the X-ray optics assembly also includes a monochromator, in particular a channel-cut crystal, and three beam paths for the X-ray beam are selectable using the switching system, wherein a first beam path in a first position of the switching system leads past the multilayer mirror and leads past the monochromator, wherein a second beam path in a second position of the switching system contains the multilayer mirror and leads past the monochromator, and wherein a third beam path in a third position of the switching system contains the multilayer mirror and contains the monochromator.

By use of the X-ray optics assembly according to the invention, a switch may be made between three beam paths to allow a particular analytical task to be processed with an adapted beam geometry or adapted X-ray optics. In all three positions of the switching system, optionally assisted by further adjustment system units of the X-ray diffractometer in which the X-ray optics assembly is installed, the emanating X-ray beam is directed onto a shared sample position. When one beam path is selected, the remaining beam paths are blocked (occluded).

After the switching, in principle no further modification measures on the X-ray optics assembly are necessary, and adjustment operations are also preferably unnecessary or minimized. Rapid switching between the different measurement geometries may thus be carried out. In the first beam path, use may be made of a particularly high level of intensity, for example in the Bragg-Brentano geometry for a powder diffraction. In the second beam path, an X-ray beam which is shaped by means of the multilayer mirror may be utilized, for example in the parallel beam geometry for stress and texture measurements, or also in grazing incidence for the targeted characterization of sample material near the surface. In the third beam path, an X-ray beam which is shaped by means of the multilayer mirror and monochromatized may be utilized for high-resolution X-ray diffraction measurements, for example for defect analysis in virtually perfect crystals such as semiconductor wafers.

The X-ray optics assembly is typically combined into a single X-ray optics component (module) which as a whole may be installed in an X-ray diffractometer. The switching typically takes place by motor and automatically, but may also be carried out manually.

In one preferred embodiment, it is provided that the switching system has a carriage which is movable relative to the multilayer mirror and has a switchable aperture system, wherein the switchable aperture system and the monochromator are situated on the carriage, and that by moving the carriage the switchable aperture system is selectively situated in the X-ray beam in order to select the first or second beam path, or the monochromator is selectively situated in the X-ray beam in order to select the third beam path.

A switch of the component situated in (or on) the X-ray beam may take place in a simple manner and in a compact space using the movable carriage. With this embodiment, a particularly high intensity at the sample may be achieved, in particular in the first beam path in the Bragg-Brentano geometry, due to the fact that the X-ray optics assembly may be situated closer to the sample on account of the compact design. The monochromator (a channel-cut crystal, for example) is displaced (upwardly, for example) for enabling the Bragg-Brentano beam path, and is not mounted as an additional component in front of the X-ray optics (i.e., not in series with the switchable aperture system). The carriage is generally motor-driven, and the travel direction (VRS) of the carriage typically extends perpendicularly with respect to the beam propagation direction. The aperture system and the monochromator are situated in the beam paths, usually behind the multilayer mirror. In addition, the switchable aperture system is typically motor-driven. The switchable aperture system may include a rotatable aperture, which is particularly compact as well. Alternatively, the switchable aperture system may, for example, also include an aperture which is movable on the carriage.

In one preferred refinement of this embodiment, the carriage is movable, via guides, between two end stops on a base body of the X-ray optics assembly, in particular the two end stops having a displaceable design. The end stops facilitate rapid and accurate positioning of the switchable aperture system and the monochromator. The positions of the switchable aperture system and of the monochromator with respect to the travel direction (VRS) of the carriage may be adjusted with displaceable end stops. The multilayer mirror is fastened to the base body.

In this regard, one refinement provides that a guide bolt is guided on or in the carriage, and is movable with respect to the carriage along a sliding direction (SRF), in parallel to a travel direction (VRS) of the carriage, and that in the sliding direction (SRF) a contact element is formed on or in the carriage, on both sides of the guide bolt, and is movable on or in the carriage in parallel to the sliding direction (SRF) and supported on the carriage via a respective first spring element. With the guide bolt, the carriage may be contacted and pressed gently, but with sufficient force, against the particular via end stop via a respective contact element and a respective first spring element, and may thus be precisely positioned without the guide bolt having to be exactly positioned relative to the end stop. In particular, the position of the end stop may also vary, while a sufficient force is still reliably exerted on the carriage for precise contact against the end stop. After the carriage reaches the end stop, the guide bolt is to be moved considerably farther, typically approximately over one-half of its possible travel path (maximum spring stroke), against the force of the first spring element, onto the end stop. A respective travel path of the contact elements with respect to the carriage, starting from a center position of the guide bolt, is preferably at least 3.0 mm. The contact elements may be designed as lock washers whose travel path on the guide bolt is delimited by locking stops; correspondingly, when the guide bolt moves from a center position, only one contact element rests, at least temporarily, against the guide bolt. This prevents the movement toward one of the end stops from being assisted by the first spring element of the oppositely situated end stop.

It is preferably provided that a drive spindle, on which a spindle nut that is guided on the base body rests, is provided on the base body of the X-ray optics assembly, and that the guide bolt is coupled to the spindle nut, in particular via a carrier which protrudes laterally from the guide bolt. The spindle mechanism is simple, robust, and inexpensive. Due to the transmission of force via the guide bolt and the first spring elements, the spindle mechanism, which as such is less precise, is also sufficient for precisely positioning the carriage.

In one advantageous embodiment, the monochromator is fastened to an adjustment unit which is supported via an articulated joint that is rotatable with at least two degrees of freedom. The rotary position of the monochromator may be adjusted (relative to the multilayer mirror or the X-ray beam emanating therefrom) via the rotatable articulated joint. The articulated joint or the rotation axes is/are preferably situated close to the monochromator or the X-ray beam, for example at a distance of 2 cm or less. The articulated joint is typically supported on a movable carriage of the X-ray optics assembly, which bears the monochromator and a switchable aperture system. The adjustment unit typically includes a retaining element on which the articulated joint is provided, and an adjustment element for adjusting the monochromator, in particular an adjustment lever that protrudes laterally from the retaining element. The rotatable articulated joint preferably has exactly two degrees of freedom (originally, or also by blocking further degrees of freedom), thus making easier adjustment possible. However, rotatability with respect to all three degrees of freedom may also be provided in order to limit the adjustment options as little as possible.

One refinement of this embodiment is particularly preferred in which the rotatable articulated joint is designed as a ball joint. Ball joints allow very precise, durable settings. The ball joint in principle is rotatable with respect to three degrees of freedom. If desired, one degree of freedom may be blocked by a suitable guide in order to simplify the adjustment.

In one preferred further development of this refinement, the adjustment unit includes a retaining element and an adjustment element, the retaining element having a ball section, a first connecting section from the ball section to the monochromator, and a second connecting section from the ball section to the adjustment element. The retaining element typically has an essentially linear design, with a ball section situated approximately in the middle and oppositely situated connecting sections ("spindle"). This further development allows favorable application of force during the adjustment, and a compact design.

Also advantageous is a refinement which provides that the adjustment unit is provided with a ball section, the ball section being situated between two joint socket elements, in particular the joint socket elements being designed as perforated plastic disks, and that the joint socket elements are pretensioned with respect to one another by means of one or more second spring elements, in particular disk springs. This design allows essentially play-free retention of the adjustment unit in a simple manner.

One refinement is particularly preferred which provides that a guide arrangement having two mutually facing guide sections is provided, between which the adjustment unit is guided with contact, so that the adjustment unit is pivotable about a first axis (y) which extends through the midpoint of the ball joint and perpendicularly with respect to the guide plane, in parallel to a guide plane which is parallel to the guide sections, in addition the adjustment unit is rotatable about a second axis (x) which extends through the midpoint of the ball joint and perpendicularly with respect to the first axis (y), and the adjustment unit rests against the guide sections at a distance from the midpoint of the ball joint with respect to the direction of the second axis (x), so that pivoting of the adjustment unit about a third axis (z) which extends through the midpoint of the ball joint and perpendicularly with respect to the first axis (y) and perpendicularly with respect to the second axis (x) is blocked.

With this refinement, the rotation of the adjustment unit may be limited to two axes (x, y) in order to simplify the adjustment. The guide sections are usually designed as guide surfaces, but may also be designed as guide edges. The guide sections are typically slightly elastically pretensioned on the adjustment unit in order to reduce the play. The guide arrangement is typically provided on the movable carriage. The first, second, and third axes (x, y, z) are oriented mutually perpendicularly with respect to one another.

The guide arrangement is advantageously designed to be rotatable about the second axis (x), the adjustment unit resting against the guide sections at a distance from the midpoint of the ball joint with respect to the direction of the third axis (z), so that when the adjustment unit rotates about the second axis (x), it also turns the guide arrangement, in particular the guide arrangement being designed with a locking sleeve. In this embodiment, the position of the first axis (y) is fixed with respect to the monochromator. This allows a particularly simple, intuitive adjustment. In addition, for large rotation angles, nonlinearities may be avoided in this design, if relevant. The guide arrangement is typically rotatably supported on the movable carriage.

Alternatively, it may be provided that the guide arrangement has a rotatably fixed design, that the adjustment unit rests against the guide sections with circular cylinder lateral surface sections, wherein a shared cylinder axis of the circular cylinder lateral surface sections extends through the midpoint of the ball joint, so that when the adjustment unit rotates about the second axis (x), the adjustment unit rotates about the shared cylinder axis with respect to the guide arrangement, in particular the guide arrangement guiding the adjustment unit in a circular cylindrical area. This design is particularly simple. The circular cylinder lateral surface sections are usually formed by oppositely situated sides of a circular cylindrical area of the adjustment unit. For guide sections which extend in the direction of the x axis, the circular cylinder lateral surface sections may also have a very short design axially; the cylinder axis then corresponds to the axis through the shared circular arc section midpoint, perpendicular to the shared plane of the circle.

In one advantageous refinement of the above embodiment, a first adjustment mechanism for pivoting the adjustment unit about a first axis (y) and a second adjustment mechanism for rotating the adjustment unit about a second axis (x) are present. A precise setting of the rotary position of the adjustment unit with respect to the two axes (x, y) may be made via the adjustment mechanisms; with regard to the first and second axes (x, y), also see the preceding refinements.

One advantageous further development of this refinement provides that the adjustment unit has an adjustment lever which protrudes essentially transversely with respect to the second axis (x), and on which the first and second adjustment mechanisms engage, the adjustment lever is deflectable via the first adjustment mechanism in a direction approximately parallel to the second axis (x), and the adjustment lever is deflectable via the second adjustment mechanism in a direction approximately parallel to the first axis (y). A simple and precise type of adjustment of the monochromator is possible with the adjustment lever. As an alternative to an adjustment lever, an adjustment wheel, for example, may be used.

In another refinement, the first adjustment mechanism and the second adjustment mechanism each press the adjustment unit with the force of a respective third spring element, in particular a tension spring, against a displaceable adjustment stop, in particular a threaded spindle or adjustment screw. Positioning of the monochromator with little play is thus possible.

The scope of the present invention also encompasses an X-ray diffractometer which includes an X-ray source, a position for a sample, an X-ray detector which is movable about the position of the sample on a circular arc, and an adjustment system with which beam paths for an X-ray beam are selectable. This embodiment is characterized in that the X-ray diffractometer also includes an above-described X-ray optics assembly according to the invention, the adjustment system of the X-ray diffractometer including at least the switching system of the X-ray optics assembly. In this arrangement, the first beam path is in a first adjustment of the adjustment system, with the switching system in the first position, the second beam path is in a second adjustment of the adjustment system, with the switching system in the second position, and the third beam path is in a third adjustment of the adjustment system, with the switching system in the third position, and in each case the X-ray beam is directed from the X-ray source to the position of the sample. By use of the X-ray diffractometer according to the invention, a switch may be quickly made between three measurement geometries, in particular by motor and in an automated manner. The changeover of the beam paths may take place by switching over the switching system, and if necessary, supplemented by switching over/adjusting further units of the adjustment system. Additional modification is not necessary; likewise, further adjustment is typically not required or is minimized.

One embodiment of the X-ray diffractometer according to the invention is particularly preferred in which the adjustment system also includes a carriage on the primary side, on which at least the X-ray source and the X-ray optics assembly are situated, and which may be moved and/or pivoted at least between a first position and a second position, in particular wherein a positional difference between the second position and the first position of the carriage on the primary side compensates for an X-ray beam change by the monochromator in the third beam path with respect to the second beam path. Similarly, for the second beam path or the second adjustment, the first position is used, and for the third beam path or the third adjustment, the second position is used. For the first beam path or the first adjustment, typically the first position is used. This design allows the use of a monochromator which changes the X-ray beam in the third beam path with respect to the second beam path on the output side of the X-ray optics assembly, in particular the use of a (single) channel-cut crystal, thus also allowing very compact designs (with a small distance between the X-ray source and the sample). A typical X-ray beam change by the monochromator is a parallel offset of the X-ray beam, which is compensated for by an oppositely directed, shared translation of the X-ray source and the X-ray optics assembly.

In one advantageous alternative embodiment, the monochromator is designed in such a way that the second beam path and the third beam path on the output side of the X-ray optics assembly extend relative to the X-ray optics assembly in an identical manner, in particular the monochromator including two channel-cut crystals in succession in the Bartels arrangement, and the adjustment system includes only the switching system of the X-ray optics assembly. This design is particularly simple with regard to the switchover, since a carriage on the primary side is not needed. However, the monochromator for this embodiment must be manufactured in a particularly precise manner.

In one preferred embodiment, it is provided that the first beam path in a Bragg-Brentano geometry, after reflection on the position of the sample, focuses the X-ray beam on the circular arc, and the second beam path and the third beam path, in each case in a parallel beam geometry, direct the X-ray beam onto the position of the sample. This design is particularly simple, in particular with a Göbel mirror as the multilayer mirror and a channel-cut crystal as the monochromator.

One alternative embodiment provides that the first beam path in a Bragg-Brentano geometry, after reflection on the position of the sample, focuses the X-ray beam on the circular arc, the second beam path in a parallel beam geometry directs the X-ray beam onto the position of the sample, and the third beam path focuses the X-ray beam on the circular arc, through the position of the sample, in particular the monochromator including a Johansson monochromator. In this design, a transmission geometry may be utilized in the third beam path.

Further advantages of the invention result from the description and the drawings. In addition, the features mentioned above and explained in greater detail below may in each case be used according to the invention, individually or collectively in any combination. The embodiments shown and described are not to be construed as an exhaustive listing, but, rather, are exemplary in nature for describing the invention.

BRIEF DESCRIPTION OF THE DRAWINGS

The invention is illustrated in the drawings and is explained in greater detail with reference to exemplary embodiments, as follows:

FIG. 8 shows a schematic top view of the adjustment unit from FIG. 7;

FIG. 9 shows a schematic stepped cross-sectional illustration of the adjustment unit from FIG. 7, along plane B from FIG. 7;

FIG. 10a shows a schematic sectional illustration of a clamping mechanism of the X-ray optics assembly from FIG. 4a, in a center position;

FIG. 10b shows the clamping mechanism from FIG. 10a, in an intermediate position upon reaching an end stop on the right side;

FIG. 10c shows the clamping mechanism from FIG. 10a, in a braced position at the end stop on the right side;

FIG. 14b shows a schematic top view of the adjustment unit from FIG. 14a.

DETAILED DESCRIPTION

Figure 1:
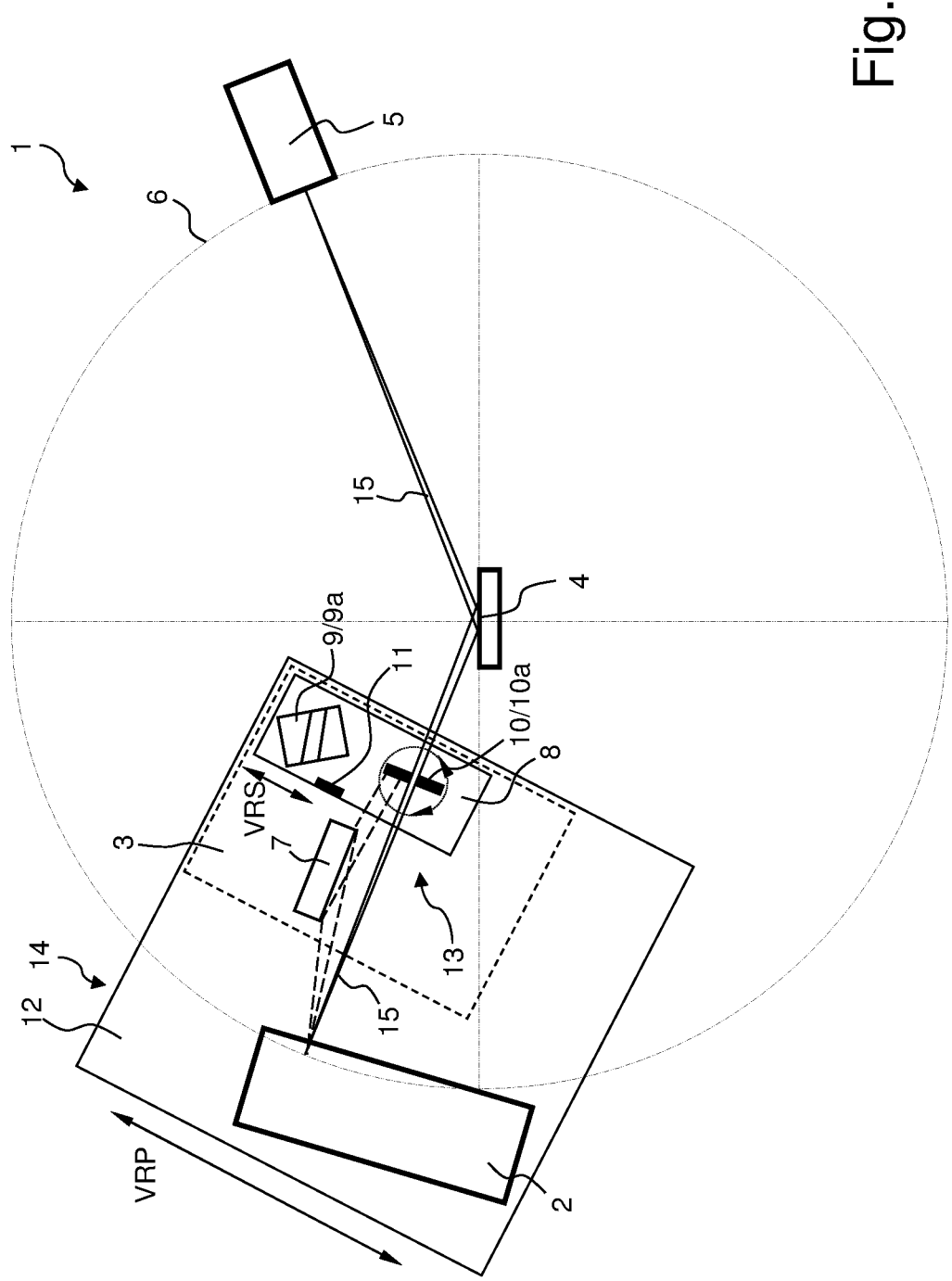
FIG. 1 shows a schematic illustration of one embodiment of an X-ray diffractometer according to the invention, in a first switching position of the X-ray optics assembly for the first beam path in the Bragg-Brentano geometry.

The present invention provides an X-ray optics assembly and an X-ray diffractometer having such an assembly, with which X-ray diffraction measurements may take place in three different measurement geometries. The switching between the measurement geometries preferably takes place in an automated manner, so that (manual) intervention in the measuring apparatus, which could possibly require readjustment of the optics, is not necessary. Within the scope of the invention, the same sample may be measured using various modes, generally without the need for an intermediate adjustment of the optics.

The measurement geometries or measuring applications preferably include the Bragg-Brentano application, typically with a motorized aperture (for example, for powder analysis, optionally in conjunction with Riedveld analysis), the application with a parallelizing Göbel mirror (for stress and texture measurements, for example), and applications in the area of high-resolution XRD, using a Göbel mirror combined with a monochromator.

The assembly may have a compact, space-saving design, so that even in the Bragg-Brentano application, the tube focus is not a very great distance from the sample to be examined. In the Bragg-Brentano measurement geometry, a preferably short distance between the tube focus and the sample is advantageous for the application.

For this purpose, it is preferably provided that the monochromator is fastened to a spindle having a lathed ball. The ball is braced between two plastic disks (joint sockets) in a holder by means of disk springs. In this ball joint, all necessary degrees of freedom have a common rotation point, thus saving installation space. The spindle is supported without play due to pretensioning. Only rotation or tilting about three axes is possible, with a corresponding application of force. Two of the three degrees of freedom are typically fixed by the bearing of an adjustment lever by means of threaded spindles and tension springs. The unused third degree of freedom is blocked via a locking sleeve. By turning on threaded spindles, the monochromator may be rotated about two axes (x and y) into the desired position with respect to the X-ray beam.

A very precise switching mechanism is possible within the scope of the invention. This is advantageous, since during the measurement the X-ray optics may be subjected to load variations, which should not influence the analysis. The invention utilizes in particular a stable, accurate adjustment device for the monochromator.

For highly accurate and reproducible positioning of the components of the X-ray optics assembly, to be switched, at the end positions of a carriage translation, a clamping mechanism is proposed which holds the carriage in the end positions with a defined force. By use of the clamping mechanism, the carriage, despite load variations, may be pressed without play against one of its two end stops with a force that is always sufficient, thus ensuring displacement of the stops in a range of ±1.5 mm, for example. In addition, the drive does not result in a "hard" impact against the end stops, so that jamming of the drive mechanism may be avoided.

X-Ray Diffractometer and Beam Paths

FIG. 1 shows a schematic view of one embodiment of an X-ray diffractometer 1 according to the invention. The X-ray diffractometer includes an X-ray source 2, such as an X-ray tube having a Cu anode, an X-ray optics assembly 3 (bordered by dashed lines), a position 4 for a sample to be measured, and an X-ray detector 5. The source focus of the X-ray tube 2 (or optionally a corresponding image of same) and the X-ray detector 5 (or optionally a corresponding detector aperture) are situated on a circular arc (measuring circle) 6 about the position 4 of the sample. The X-ray source 2 and/or the X-ray detector 5 may be moved on the circular arc 6 in a customary manner in order to measure a sample, and/or the sample may be rotated for this purpose.

The X-ray optics assembly 3 includes a multilayer mirror 7, which is designed here as a parallelizing Goebel mirror, and a carriage 8 which is movable with respect to the multilayer mirror 7. A monochromator 9, which is designed here as a channel-cut crystal 9a, and a switchable aperture system 10, which is designed here with a rotatable aperture 10a, are situated on the carriage 8. In addition, an auxiliary aperture 11 is situated on the carriage 8.

The rotatable aperture 10a is rotatable between a first rotary position (as illustrated in FIG. 1) and a second rotary position (see FIG. 2, described below). The carriage 8 is movable in a travel direction VRS between a first movement position (as illustrated in FIG. 1) and a second movement position (see FIGS. 3a, 3b, described below). In the illustrated first movement position, the aperture system 10 is situated in the beam path of the X-ray light emanating from the X-ray source 2. The rotary position of the rotatable aperture 10a and the movement position of the carriage 8 define the position of a switching system 13 of the X-ray optics assembly 3 for selecting a beam path for the X-ray optics assembly 3.

In the embodiment shown, the X-ray source 2 and the X-ray optics assembly 3 are also situated on a shared carriage 12 on the primary side, which in the present case is movable between a first position (as illustrated in FIG. 1) and a second position (see FIG. 3a, described below) in a travel direction VRP. The position of the carriage 12 on the primary side and the position of the switching system 13 define as a whole the adjustment of an adjustment system 14 of the X-ray diffractometer 1 for selecting a beam path for the X-ray diffractometer 1.

In the situation shown in FIG. 1, the adjustment system 14 is in a first adjustment, with the carriage 12 on the primary side in the first position and the switching system 13 in a first position, the carriage 8 being in the first movement position, which is at the top here. X-ray radiation of a first beam path 15 emanating from the X-ray source 2 passes through a central gap in the rotatable X-ray aperture 10a in the first rotary position; it is noted that the beam width may be set to a certain extent by (slightly) rotating the rotatable aperture 10a. The X-ray radiation is then reflected at the position 4 of the sample, and is correspondingly focused on the X-ray detector 5 or the circular arc 6 (Bragg-Brentano geometry). X-ray radiation that is reflected on the multilayer mirror 7 is blocked by a portion of the switchable aperture system 10.

Figure 2:
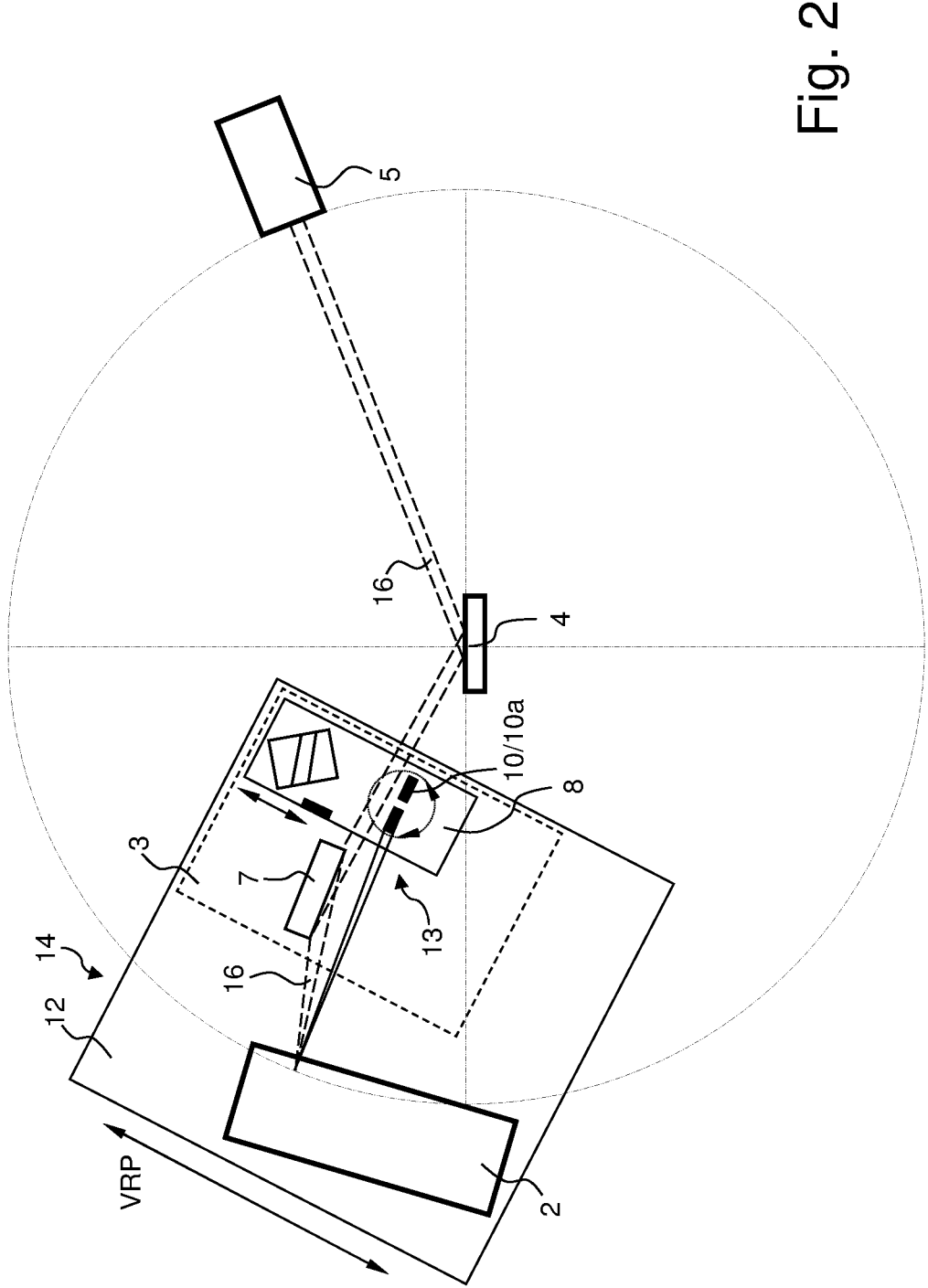
FIG. 2 shows the X-ray diffractometer from FIG. 1, in a second switching position of the X-ray optics assembly for the second beam path in the parallel beam geometry.

In the situation shown in FIG. 2, the adjustment system 14 is in a second adjustment with the carriage 12 on the primary side still in the first position, but with the switching system 13 in a second position, the carriage 8 being in the first movement position, at the top here. X-ray radiation of a second beam path 16 emanating from the X-ray source 2 is reflected on the multilayer mirror 7 and thus parallelized, and passes the rotatable aperture 10a in a second rotary position and arrives at position 4 of the sample. At that location the X-ray beam is reflected and arrives at the X-ray detector 5 (parallel beam geometry without a monochromator). X-ray radiation which arrives at the aperture system 10 directly from the X-ray source is blocked by the aperture system 10.

Figure 3A:
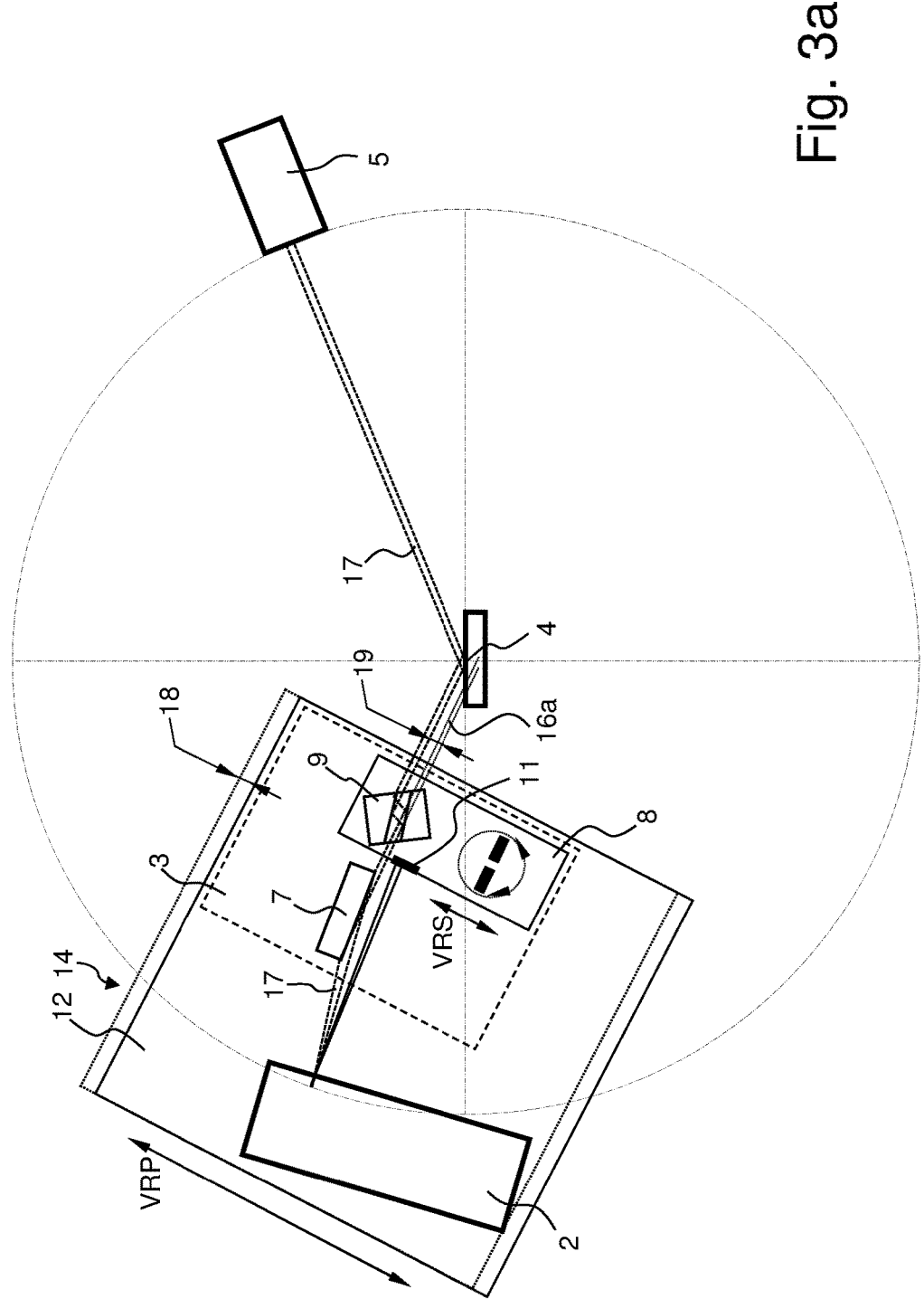
FIG. 3a shows the X-ray diffractometer from FIG. 1, in a third switching position of the X-ray optics assembly for the third beam path in the parallel beam geometry, with a carriage on the primary side in a displaced position.

In the situation shown in FIG. 3a, the adjustment system 14 is in a third adjustment, with the carriage 12 on the primary side in a second position, which is shifted slightly downwardly here with respect to the first position in the travel direction VRP (see dotted-line carriage contour). In addition, the switching system 13 of the X-ray optics assembly 3 is in a third position; for this purpose the carriage 8 has been brought into a second movement position, which is shifted slightly downwardly here, in the travel direction VRS. X-ray radiation of a third beam path 17 emanating from the X-ray source 2 is reflected on the multilayer mirror 7 and thus parallelized, and enters the monochromator 9. After being reflected twice on the mutually facing, parallel crystal faces of the monochromator, the X-ray beam strikes the position 4 of the sample. At that location the X-ray beam is reflected and arrives at the X-ray detector 5 (parallel beam geometry with a monochromator). X-ray radiation which emanates directly from the X-ray source 2 is blocked here by the auxiliary aperture 11.

The shift 18 of the carriage 12 on the primary side compensates for an offset 19 of the third beam path 17 with respect to an imaginary beam path 16a (indicated by a finely dotted line, similarly as for the second beam path), without a monochromator, on the output side of the X-ray optics assembly 3, so that the third beam path 17 also arrives centrally at the position 4 of the sample.

Figure 3B:
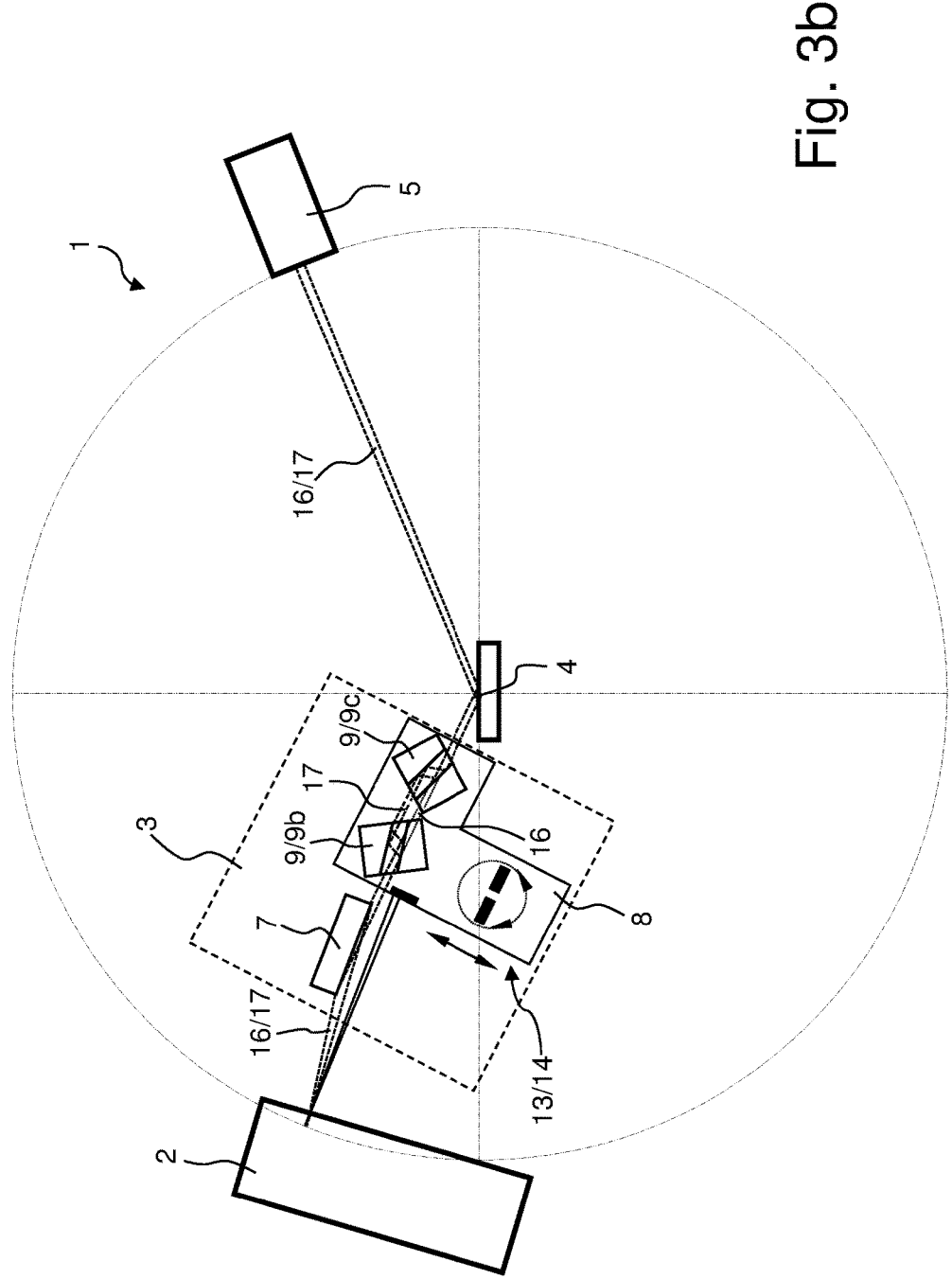
FIG. 3b shows the X-ray diffractometer in an illustration similar to FIG. 1, in a third switching position of the X-ray optics assembly for the third beam path in the parallel beam geometry, with a double channel-cut crystal.

FIG. 3b shows an alternative embodiment of an X-ray diffractometer 1 according to the invention, illustrated similarly as in FIGS. 1, 2, and 3a; therefore, only the important differences are explained in greater detail. In this embodiment, the adjustment system 14 of the X-ray diffractometer 1 includes only the switching system 13 of the X-ray optics assembly 3; in particular, a carriage on the primary side is not necessary.

In the third adjustment of the adjustment system 14, i.e., in the third position of the switching system 13, the carriage 8 is once again in the second movement position. The X-ray beam of the third beam path 17 which is reflected on the multilayer mirror 7 and parallelized arrives here at a monochromator 9, which includes a first channel-cut crystal 9b and a second channel-cut crystal 9c situated in succession (Bartels arrangement), so that an offset of the X-ray beam by the first channel-cut crystal 9b is exactly cancelled out by the second channel-cut crystal 9c. For this purpose, the two channel-cut crystals 9b, 9c are in a fixed orientation relative to one another, and both move with the carriage 8; typically, the two channel-cut crystals 9b, 9c are separately adjustable on the carriage 8. The third beam path 17 therefore differs from the second beam path 16 (illustrated by a finely dotted line) only over a small segment; in particular, the second beam path 16 and the third beam path 17 extend in the same way on the output side of the X-ray optics assembly 3.

X-Ray Optics Assembly

Figure 4A:
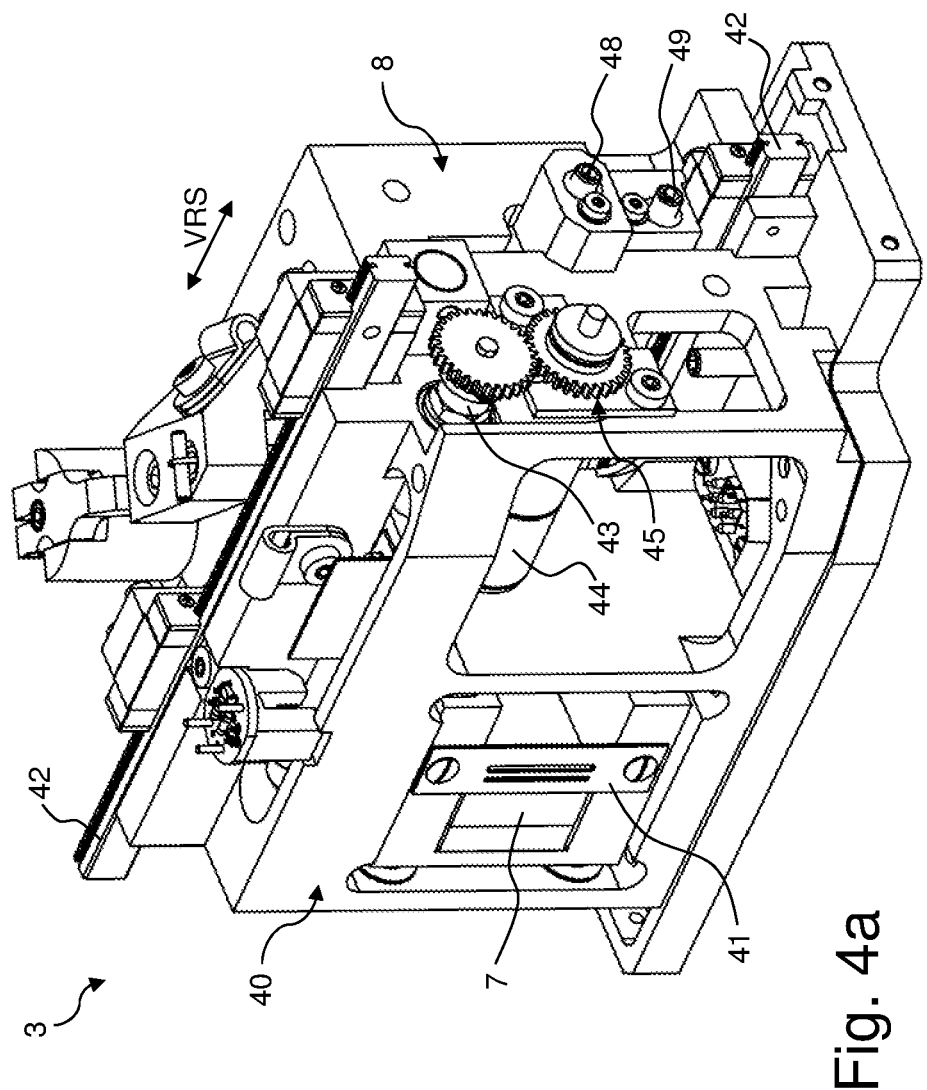
FIG. 4a shows a schematic perspective view of one embodiment of an X-ray optics assembly according to the invention, with a movable carriage on a base body, with the base body in the foreground.
Figure 4B:
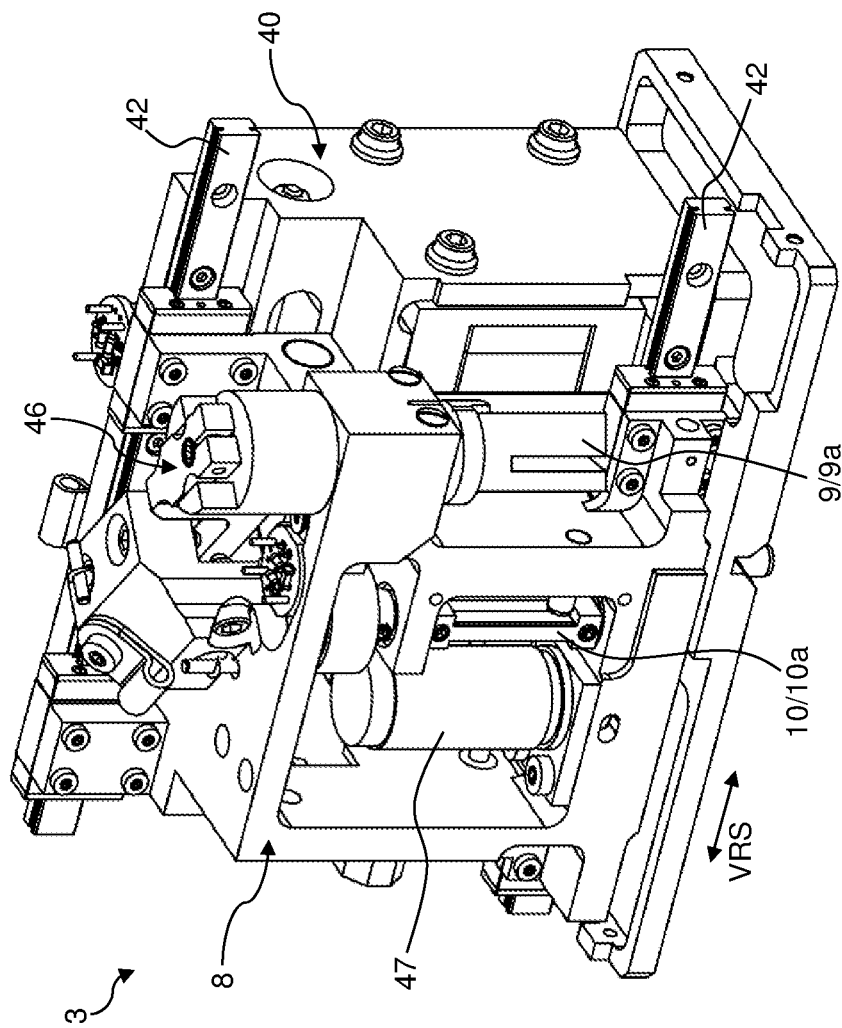
FIG. 4b shows a schematic perspective view of the X-ray optics assembly from FIG. 4a, with the carriage in the foreground.

One embodiment of an X-ray optics assembly 3 according to the invention, which may be installed in the X-ray diffractometer in FIGS. 1, 2, 3a, is illustrated in FIG. 4a in a schematic oblique view with a base body 40 in the foreground, and in FIG. 4b in a schematic oblique view with the carriage 8 in the foreground.

The multilayer mirror 7 is supported on the base body 40; at the input side of the multilayer mirror 7 a double slit aperture 41 is also provided, with one slit for the first beam path and another slit for the second and third beam paths. Guides 42 on which the carriage 8 may move along the travel direction VRS are provided on the base body 40. A drive spindle 43 which is driven via a motor 44 and a gear 45 is also provided on the base body 40. The drive spindle drives a spindle nut, which in turn is coupled to a guide bolt in the carriage 8 (concealed in FIGS. 4a, 4b; see FIG. 5, described below).

The monochromator 9, which is designed as a channel-cut crystal 9a, is supported and displaceable on the carriage 8 via an adjustment unit 46 (largely concealed; also see FIGS. 7, 8, and 9, described below). The displaceable aperture system 10, which is designed here with a rotatable aperture 10a, is also situated on the carriage 8. The rotatable aperture 10a may be rotated via a motor 47 and a gear (concealed in FIGS. 4a, 4b).

The X-ray optics assembly 3 also has two fine thread spindles 48, 49 via which the displaceable end stops for the carriage 8 are formed (see FIG. 6, described below).

Figure 4C:
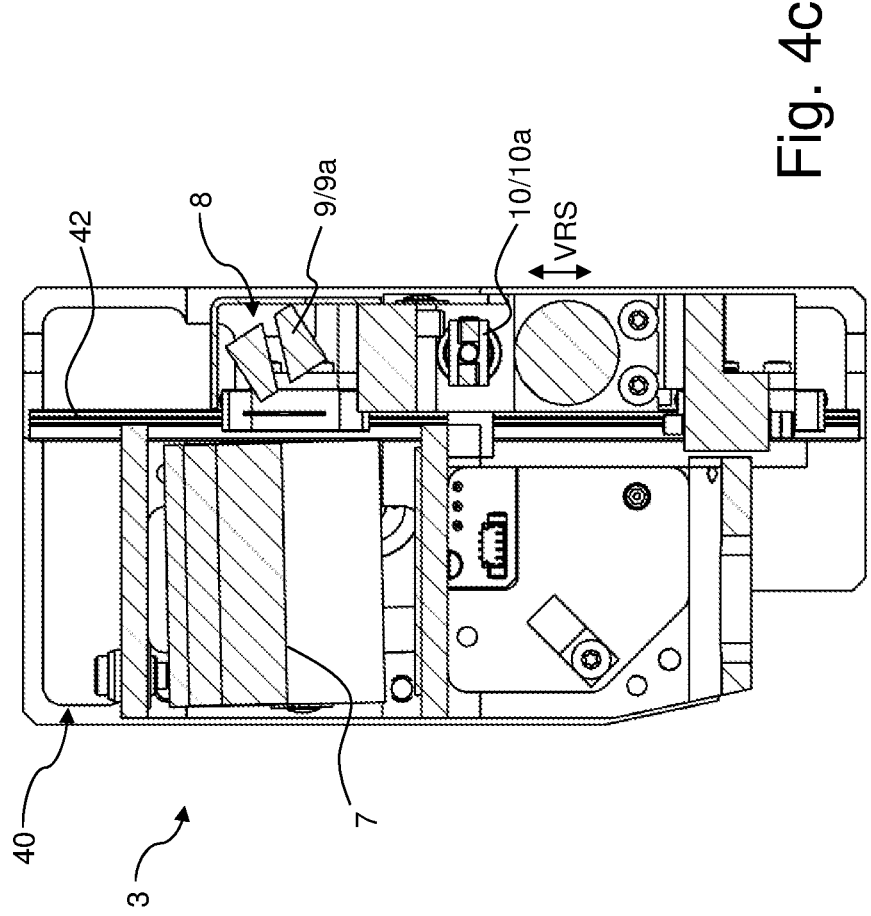
FIG. 4c shows a schematic cross section of the X-ray optics assembly from FIG. 4a, at the level of the beam paths.

FIG. 4c illustrates a cross section of the X-ray optics assembly 3 from FIG. 4a, 4b at the level of the beam paths. In the illustrated second movement position of the carriage 8 at the guides 42 of the base body 40, an X-ray beam (not illustrated) may be reflected on the multilayer mirror 7 (and thus parallelized), and may then further propagate through the channel-cut crystal 9a to the sample position (not illustrated). The rotatable aperture 10a in this case has moved out of the beam path.

Figure 5:
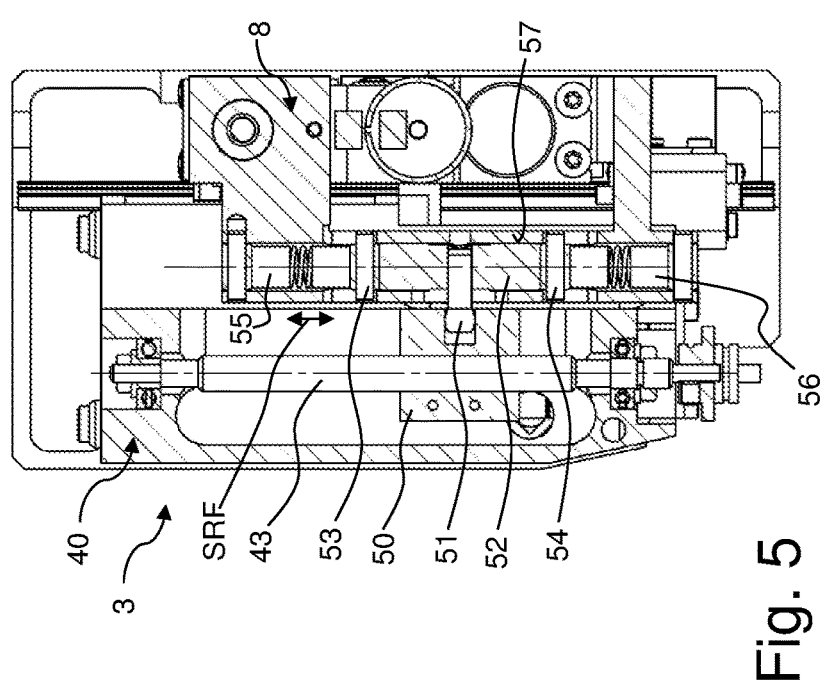
FIG. 5 shows a schematic cross section of the X-ray optics assembly from FIG. 4a, at the level of a drive spindle.

FIG. 5 shows a cross section of the X-ray optics assembly 3 from FIGS. 4a, FIG. 4b at the level of the drive spindle 43. A spindle nut 50 which is guided on the base body 40 in a rotatably fixed manner rests on a thread (not illustrated in greater detail) of the drive spindle 43, so that the spindle nut 50 moves along the drive spindle axis (from top to bottom in FIG. 5) when the drive spindle 43 rotates.

The spindle nut 50 is coupled to a guide bolt 52 via a carrier 51 which protrudes into a recess in the spindle nut 50, and the guide bolt in turn is movable in the carriage 8 in a corresponding borehole 57 in the carriage 8 along a sliding direction SRF. The carrier 51 is fixedly connected to the guide bolt 52, and protrudes laterally from same. The guide bolt 52 may be moved in the borehole 57 in the carriage 8 against contact elements 53, 54, which likewise are movable in the borehole 57 in the sliding direction SRF. The contact elements 53, 54 are supported on the carriage 8 via first spring elements 55, 56 (the clamping mechanism of the carriage 8 in FIGS. 10a through 10c is described in greater detail below).

Figure 6:
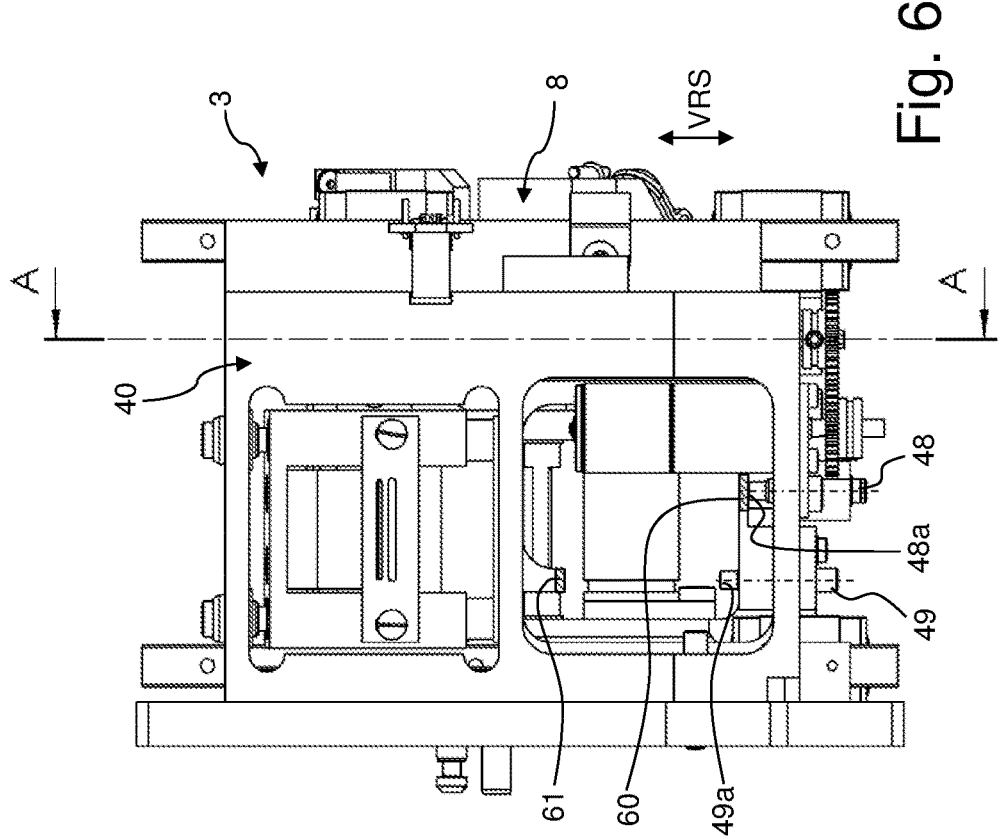
FIG. 6 shows a schematic side view of the X-ray optics assembly from FIG. 4a, on the carriage.

FIG. 6 illustrates the displaceable mutual stops (end stops) of the base body 40 and the carriage 8 by means of the fine thread spindles 48, 49, in a side view of the X-ray optics assembly 3.

The first fine thread spindle (or adjustment screw) 48 is supported in the base body 40, and with its front end 48a delimits the travel path of the carriage 8 downwardly in FIG. 6 by resting against a stop element 60 (illustrated in crosshatch) which is formed on the carriage 8. The second movement position of the carriage 8 with respect to the base body 40 may be defined or changed (and thus, the position of the monochromator may be adjusted) by screwing the fine thread spindle 48 in or out. In the movement position of the carriage 8 shown, the stop element 60 just rests against the front end 48a.

The second fine thread spindle (or adjustment screw) 49 is supported in the carriage 8. The front end 49a of the second fine thread spindle delimits the travel path of the carriage 8 upwardly in FIG. 6 by resting against a stop element 61 (illustrated in crosshatch) which is formed on the base body 40. The first movement position of the carriage 8 with respect to the base body 40 may be defined or changed (and thus, the position of the rotatable aperture may be adjusted) by screwing the fine thread spindle 49 in or out. In the movement position of the carriage 8 shown, the stop element 61 is just situated at a great distance from the front end 49a.

Due to the bearing of a fine thread spindle 48 in the base body 40 and of a fine thread spindle 49 in the carriage 8, it is possible to situate the fine thread spindles 48, 49 for both end stops on the same side of the X-ray optics assembly 3 (at the bottom here), which facilitates the adjustment.

FIG. 6 also shows the section plane A in FIG. 5.

Figure 7:
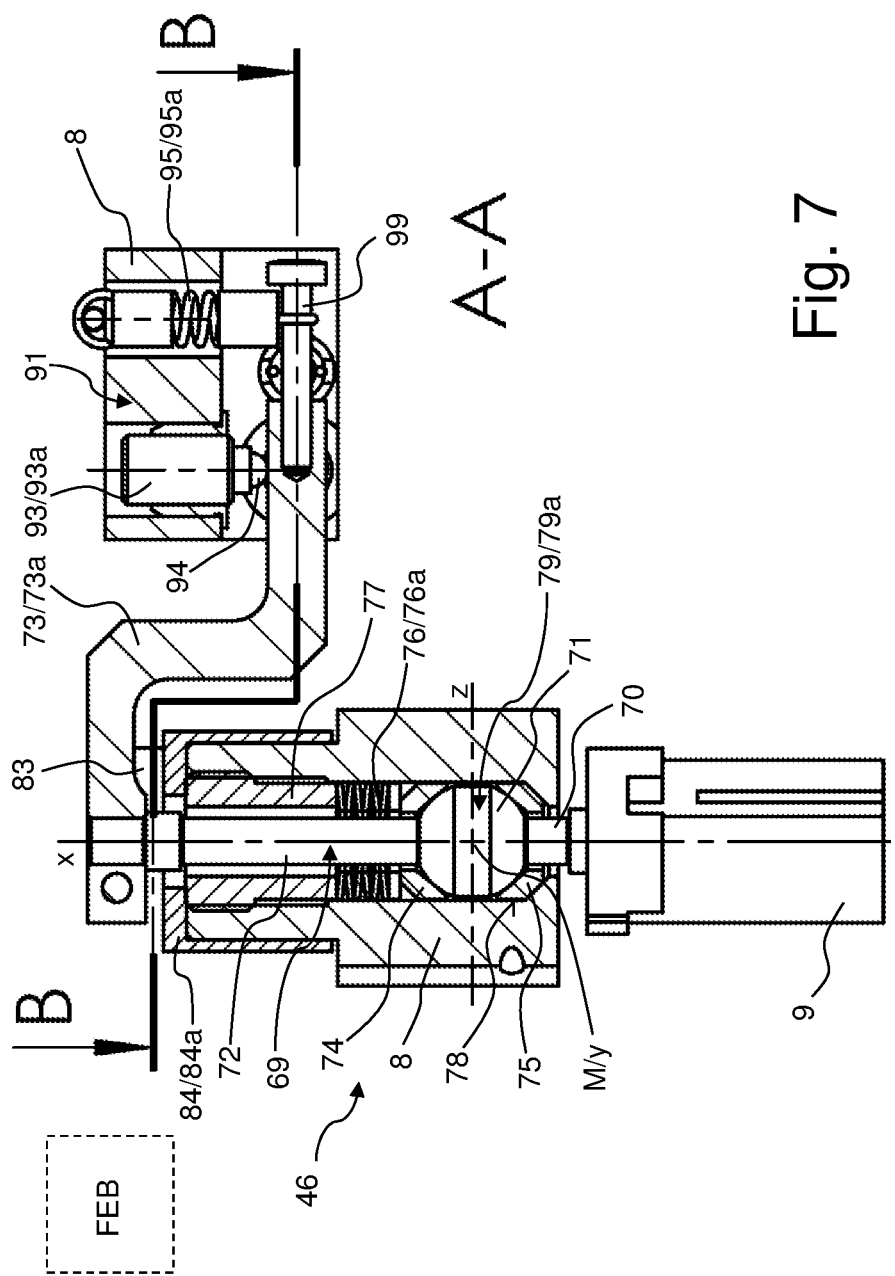
FIG. 7 shows a schematic longitudinal sectional illustration of the adjustment unit of the X-ray optics assembly from FIG. 4a, including adjustment mechanisms, with a rotatable locking sleeve.

FIG. 7 shows a schematic longitudinal section of the adjustment unit 46 of the X-ray optics assembly according to the invention from FIGS. 4a, FIG. 4b, on which the monochromator 9 is held. The adjustment unit 46 includes a first connecting section 70 from the monochromator 9 to a ball section 71 of the adjustment unit 46, with which the adjustment unit is supported. Also provided is a second connecting section 72, which leads from the ball section 71 to the fastening of an adjustment element 73 of the adjustment unit 46; the connecting sections 70, 72 are situated opposite from one another and extend coaxially, with the midpoint M of the ball section 71 on their shared component axis. The connecting sections 70, 72 and the ball section 71 are also collectively referred to as a retaining element 69. The adjustment element 73 is designed here as a laterally protruding adjustment lever 73a. The ball section 71, and for the most part also the connecting sections 70, 72, extend in a borehole 78 in the carriage 8.

The ball section 71 is clamped between two mutually facing joint socket elements 74, 75, here in the form of beveled, perforated plastic disks. The lower joint socket element 75 rests against the carriage 8 at the lower end of the borehole 78, and the upper joint socket element 74 is pressed onto the ball section 71 by means of second spring elements 76, in the present case multiple stacked disk springs 76a, so that the ball section 71 is held between the joint socket elements 74, 75 virtually without play. The disk springs 76a are supported on an immovable fixing sleeve 77 which is pressed into the borehole 78.

Due to the articulated joint 79, namely, the ball joint 79a, which is formed by the ball section 71 and the joint socket elements 74, 75, the monochromator 9 in principle could be rotated or pivoted with respect to three orthogonal axes x, y, z (three degrees of freedom) which extend through the midpoint M of the ball section 71, by means of the adjustment unit 46. However, in the design shown in FIG. 7, one degree of freedom, namely, the rotation about the z axis, is blocked, as is also apparent from the top view in FIG. 8 and the stepped sectional illustration in FIG. 9 (see section plane B in FIG. 7).

Mutually facing, parallel guide sections 82, 83 of a guide arrangement 84, which is designed here as a locking sleeve 84a, rest against mutually facing, parallel side surfaces 80, 81 of the adjustment lever 73a. The adjustment lever 73a or the adjustment unit 46 may be pivoted in parallel to a guide plane FEB, i.e., about the y axis, along the guide sections 82, 83; the y axis extends perpendicularly with respect to the guide plane FEB.

The locking sleeve 84a in turn is supported on the carriage 8 so that the locking sleeve is rotatable about the x axis. Correspondingly, the adjustment lever 73a or the adjustment unit 46 as a whole may be pivoted about the x axis; the x axis extends in parallel to the guide plane FEB. The side surfaces 80, 81, which are situated in the direction of the z axis next to (at a distance from) the x axis, thus carry the guide arrangement 84 along.

However, the guide arrangement 84 with the guide sections 82, 83 blocks pivoting of the adjustment unit 46 about the z axis. The guide sections 82, 83 are situated at a distance from the axis (in the present case, in the direction of the x axis).

It is pointed out that in addition, the second connecting section 72, having a circular cross section, protrudes through an elongated hole 85 in the locking sleeve 84a which is elongated in the direction of the z axis, and which rests on two sides against the second connecting section 72. The adjustment unit 46 is additionally guided in this way.

A first adjustment mechanism 91 and a second adjustment mechanism 92 are also shown, with reference to FIGS. 7, 8, and 9.

The first adjustment mechanism 91, which is particularly clearly apparent in FIG. 7, has a third spring element 95, which is designed here as a tension spring 95a, and which pulls the adjustment lever 73a via an extension screw 99 against a displaceable adjustment stop 93, in the present case a threaded spindle 93a, on the carriage 8. The lower, protruding portion of the adjustment lever 73a may be moved essentially in parallel to the x axis by displacing the threaded spindle 93a, thus bringing about a rotation of the adjustment unit 46 about the y axis. It is noted that the lower end 94 of the threaded spindle 93a has a spherical design here to facilitate mutual sliding of the threaded spindle 93a and the adjustment lever 73a when the latter is pivoted.

The second adjustment mechanism 92, which is particularly clearly apparent in FIG. 9, has a third spring element 96, which is designed here as a tension spring 96a, and which pulls the adjustment lever 73a via the extension screw 99 against a displaceable adjustment stop 97, in the present case a threaded spindle 97a, on the carriage 8. The lower, protruding portion of the adjustment lever 73a may be moved essentially in parallel to the y axis by displacing the threaded spindle 97a, thus bringing about a rotation of the adjustment unit 46 about the x axis. It is noted that the front end 98 of the threaded spindle 97a has a spherical design here to facilitate mutual sliding of the threaded spindle 97a and the adjustment lever 73a when the latter is pivoted.

Figure 11:
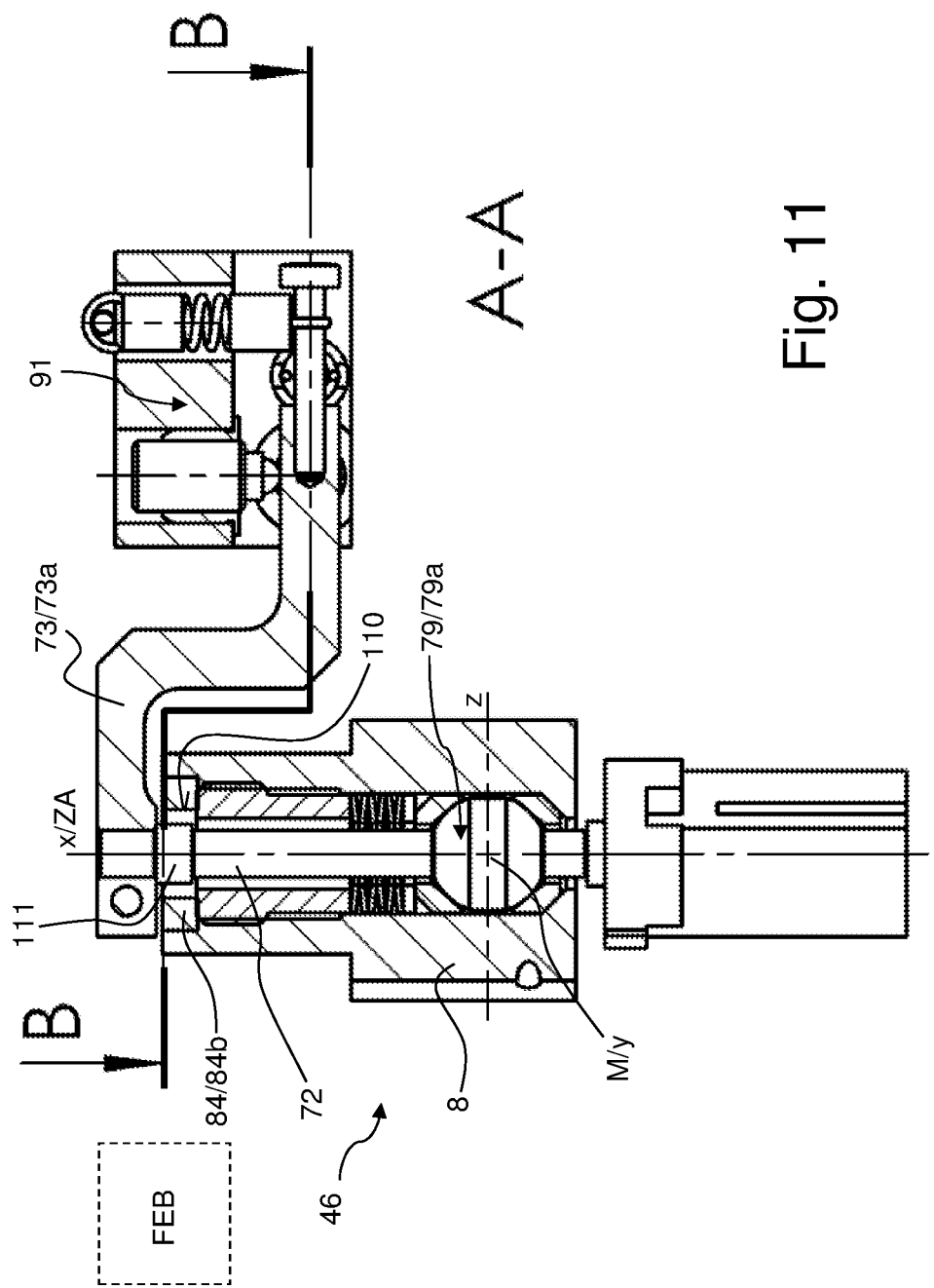
FIG. 11 shows a longitudinal sectional illustration of an alternative adjustment unit for an X-ray optics assembly according to the invention, including adjustment mechanisms, with a fixed lock washer.
Figure 12:
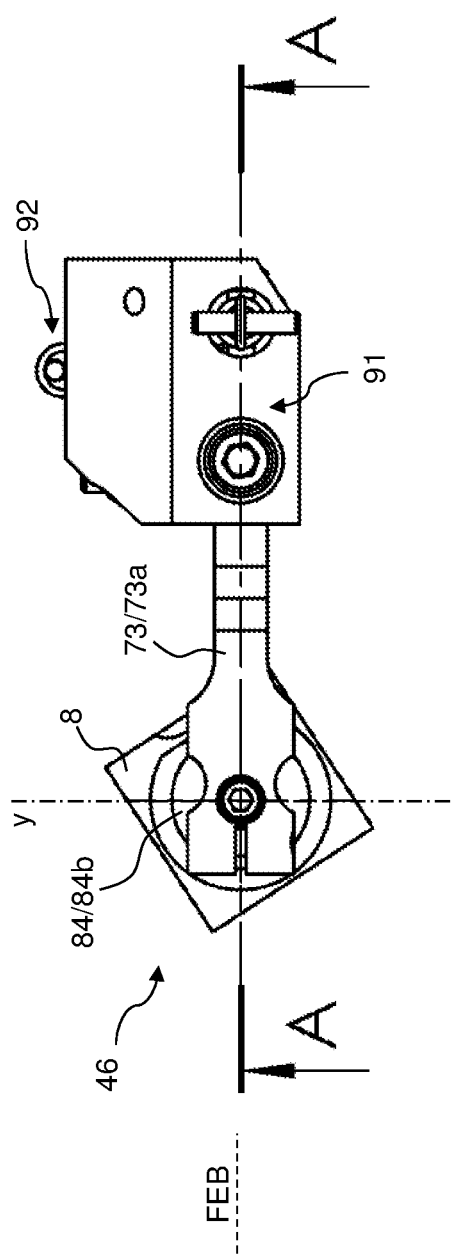
FIG. 12 shows a schematic top view of the adjustment unit from FIG. 11.
Figure 13:
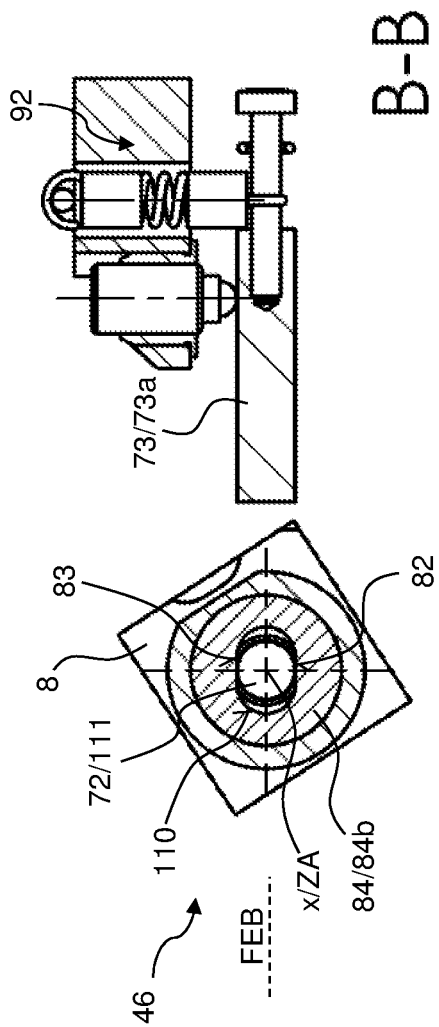
FIG. 13 shows a schematic stepped cross-sectional illustration of the adjustment unit from FIG. 11, along plane B from FIG. 11.

An alternative embodiment of the guide arrangement 84 for an adjustment element 46 is illustrated in FIG. 11 (in a longitudinal section), FIG. 12 (in a top view), and FIG. 13 (in a stepped cross section; see plane B in FIG. 11), which largely correspond to the illustrations in FIGS. 7, 8, and 9, so that only the important differences are discussed here.

The guide arrangement 84 is designed here as a rotatably fixed lock washer 84b, provided with an elongated hole 110, in the carriage 8. The elongated hole 110 extends in a direction in parallel to the z axis. The mutually facing parallel longitudinal sides of the elongated hole 110 form guide sections 82, 83 which rest against a circular cylindrical area 111 of the adjustment unit 46 on both sides. It is noted that it is sufficient for the adjustment unit 46 to rest against the guide sections 82, 83 with two sufficiently large circular cylinder lateral surface sections, although a circumferential circular cylindrical area 111 (into which the necessary circular cylinder lateral surface sections are integrated) is easier to manufacture. The circular cylindrical area 111 is formed here on the second connecting section 72. A cylinder axis ZA of the circular cylindrical area 111 extends coaxially with respect to the x axis.

The adjustment unit 46 is pivotable in the elongated hole 111 in parallel to the guide plane FEB, i.e., about the y axis, along the guide sections 82, 83. In addition, the adjustment unit 46 is rotatable about the x axis, i.e., about the cylinder axis ZA. In contrast, pivoting about the z axis is blocked due to the adjustment unit 46 resting against the guide sections 82, 83, which are situated at a distance from the z axis (in the present case, in the x direction).

The actuation of the adjustment element 73, which once again is designed here as an adjustment lever, may take place in a similar manner via adjustment mechanisms 91, 92, as illustrated in FIGS. 7, 8, and 9.

FIGS. 10a through 10c illustrate a clamping mechanism via which the carriage 8 of the X-ray optics assembly according to the invention from FIGS. 4a, 4b may be moved with respect to the base body between end stops 100, 101, along a travel direction VRS. It is noted that the end stops 100, 101 are formed via fine thread spindles 48, 49, for example, and are only schematically illustrated in FIGS. 10a through 10c.

FIG. 10a shows the carriage 8 initially in a center position. The guide bolt 52 is displaceable in the borehole 57 in the carriage 8 along a sliding direction SRF which extends in parallel to the travel direction VRS of the carriage 8. In addition, the first spring elements 55, 56, which are clamped between end elements 102, 103 fixed in the carriage 8, and contact elements 53, 54 which are movable in the sliding direction SRF, are also situated in the borehole 57. In the center position shown, the contact elements 53, 54 press lightly against the guide bolt 52 from both sides in the axial direction; the first spring elements 55, 56 are in their essentially completely relaxed position. The guide bolt 52 includes the carrier 51, which protrudes downwardly in FIG. 10a, via which force may be transmitted to the guide bolt 52 from the drive spindle (not illustrated; see FIG. 5), or via which the guide bolt 52 may be moved in the sliding direction SRF.

When the guide bolt 52 is now moved to the right, for example, by means of the drive spindle, the carriage 8 is initially simply carried along in the travel direction VRS, and in the absence of a resistance to the carriage 8, the first spring elements 55, 56 and the position of the guide bolt 52 in the carriage 8 remain essentially unchanged until the carriage 8 ultimately just reaches the end stop 101 (intermediate position; see FIG. 10b).

To achieve play-free, precise positioning of the carriage 8 on the end stop 101, the guide bolt 52 is moved a short distance farther toward the end stop 101 after reaching the end stop 101; see the spring deflection EF in FIG. 10c (braced position). It is possible only for the guide bolt 52 to move in the borehole 57 in the carriage 8 in the sliding direction SRF, but not for the carriage 8 to move in the travel direction VRS. The guide bolt 52 pushes the contact element 54 to the right, and the first spring element 56 on the right side is compressed against its elastic force. The carriage 8 is pressed against the end stop 101 via the end element 103, corresponding to the elastic force of the first spring element 56. The elastic force (or pressing force) is a function of the spring constant of the first spring element 56, and is also approximately proportional to the spring deflection EF.

If the spring deflection EF is not exactly reproducible, for example due to play in the drive spindle, this only slightly changes the pressing force with which the carriage 8 is pressed against the end stop 101, and play-free contact of the carriage 8 against the end stop 101 is still maintained. A slight change in the spring deflection EF due to a fine adjustment of the position of the end stop 101 (in the case of a displaceable end stop) also has no effect on the play-free hold of the carriage on the end stop 101.

It is noted that the contact elements 53, 54 in the shown embodiment are delimited in their travel path in the carriage 8 by elongated holes 105 by means of transverse bolts 104, in particular on the guide bolt 52 ("locking elements" 53, 54). The contact element 53 loses contact with the guide bolt 52 due to a locking stop on the guide bolt side when a small portion (typically less than 20%) of the spring deflection EF is traversed by the guide bolt 52. A mutual cancellation of the effects of the spring elements 55, 56 when the guide bolt 52 moves is largely prevented in this way.

The spring deflection EF is typically selected or planned as an approximation (for example, by controlling the drive spindle) in such a way that it is approximately one-half the spring stroke FH that is available due to the elongated holes 105, in order to provide a preferably large tolerance in the (actual) setting of the spring deflection EF. The spring stroke FH and the spring deflection EF are preferably designed in such a way that the carriage 8 in the end position (at the end stop 100, 101) may be displaced by up to ±1.5 mm and still act with sufficient pressing force on the carriage 8; for this purpose, for example the spring stroke FH may be at least 4.0 mm, and the spring deflection EF may be selected to be at least 2.0 mm.

Figure 14A:
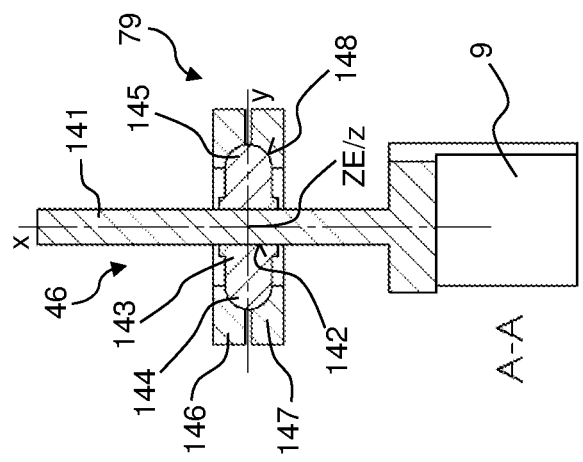
FIG. 14a shows a schematic longitudinal sectional illustration of another adjustment unit for an X-ray optics assembly according to the invention, with a joint pin.
Figure 14B:
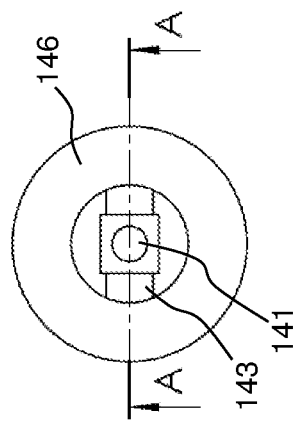

FIG. 14a (in a longitudinal section) and FIG. 14b (in a top view) illustrate an alternative design of an articulated joint 79 of an adjustment unit 46 which at the lower end holds a monochromator 9. In this articulated joint 79, a retaining element 141 is fixedly held in the borehole 142 in a joint pin 143. The joint pin 143 has spherical rounded ends 144, 145, and is held with contact (clamped) between two disk rings 146, 147, which in turn are fastened to the carriage (not illustrated). On their side facing the joint pin 143, the disk rings 146, 147 each have a circumferential cutout 148 with a circular arc cross section.

Accordingly, the adjustment unit 46 may rotate about the x axis, which extends along the axis of the retaining element 141, and also about the y axis, which extends along the axis of the joint pin 143. However, pivoting about the z axis (perpendicular to the plane of the drawing, through the center ZE of the joint pin 143) is blocked.

An adjustment element such as an adjustment lever (not illustrated) may be fastened to the upper end of the retaining element 141.

The invention claimed is:

1. An X-ray optics assembly for an X-ray diffractometer, comprising:
 a multilayer mirror;
 a monochromator; and
 a switching system with selectable beam paths for an X-ray beam, such that a first beam path in a first position of the switching system bypasses the multilayer mirror and the monochromator, a second beam path in a second position of the switching system contains the multilayer mirror and bypasses the monochromator, and a third beam path in a third position of the switching system contains the multilayer mirror and the monochromator.

2. The X-ray optics assembly according to claim 1, wherein the switching system has a carriage which is movable relative to the multilayer mirror and has a switchable aperture system, wherein the switchable aperture system and the monochromator are situated on the carriage, and wherein by moving the carriage the switchable aperture system is selectively situated in the X-ray beam in order to select the first or second beam path, or the monochromator is selectively situated in the X-ray beam in order to select the third beam path.

3. The X-ray optics assembly according to claim 2, wherein the carriage is movable via guides between two end stops on a base body of the X-ray optics assembly.

4. The X-ray optics assembly according to claim 3, wherein a guide bolt is guided on or in the carriage, and is movable with respect to the carriage along a sliding direction (SRF), in parallel to a travel direction (VRS) of the carriage, and wherein in the sliding direction (SRF) a contact element is formed on or in the carriage, on both sides of the guide bolt, and is movable on or in the carriage in parallel to the sliding direction (SRF) and supported on the carriage via a respective first spring element.

5. The X-ray optics assembly according to claim 4, wherein a drive spindle, on which a spindle nut that is guided on the base body rests, is provided on the base body of the X-ray optics assembly, and the guide bolt is coupled to the spindle nut.

6. An X-ray diffractometer comprising:
 an X-ray source;
 a position for a sample;
 an X-ray detector which is movable about the position of the sample on a circular arc;
 an adjustment system with selectable beam paths for an X-ray beam; and
 the X-ray optics assembly according to claim 1, wherein the adjustment system of the X-ray diffractometer includes at least the switching system of the X-ray optics assembly, such that the first beam path in a first adjustment of the adjustment system, with the switching system in the first position, the second beam path in a second adjustment of the adjustment system, with the switching system in the second position, and the third beam path in a third adjustment of the adjustment system, with the switching system in the third position, in each case direct the X-ray beam from the X-ray source to the position of the sample.

7. The X-ray diffractometer according to claim 6, wherein the adjustment system also includes a carriage on the primary side on which at least the X-ray source and the X-ray optics assembly are situated, and which is configured to be moved and/or pivoted at least between a first position and a second position.

8. The X-ray diffractometer according to claim 6, wherein the monochromator is designed in such a way that the second beam path and the third beam path on the output side of the X-ray optics assembly extend relative to the X-ray optics assembly in an identical manner, and the adjustment system includes only the switching system of the X-ray optics assembly.

9. The X-ray diffractometer according to claim 6, wherein the first beam path in a Bragg-Brentano geometry, after reflection on the position of the sample, focuses the X ray beam on the circular arc, and the second beam path and the third beam path, in each case in a parallel beam geometry, direct the X-ray beam onto the position of the sample.

10. The X-ray diffractometer according to claim 6, wherein the first beam path in a Bragg-Brentano geometry, after reflection on the position of the sample, focuses the X ray beam on the circular arc, the second beam path in a parallel beam geometry directs the X-ray beam onto the position of the sample, and the third beam path focuses the X-ray beam on the circular arc, through the position of the sample.

11. An X-ray optics assembly for an X-ray diffractometer, comprising:
- a multilayer mirror;
- a monochromator; and
- a switching system with selectable beam paths for an X-ray beam, such that a first beam path in a first position of the switching system bypasses the multilayer mirror and the monochromator, a second beam path in a second position of the switching system contains the multilayer mirror and bypasses the monochromator, and a third beam path in a third position of the switching system contains the multilayer mirror and the monochromator, wherein the monochromator is fastened to an adjustment unit which is supported via an articulated joint that is rotatable with at least two degrees of freedom.

12. The X-ray optics assembly according to claim 11, wherein the switching system has a carriage which is movable relative to the multilayer mirror and has a switchable aperture system, wherein the switchable aperture system and the monochromator are situated on the carriage, and wherein by moving the carriage the switchable aperture system is selectively situated in the X-ray beam in order to select the first or second beam path, or the monochromator is selectively situated in the X-ray beam in order to select the third beam path.

13. The X-ray optics assembly according to claim 11, wherein the rotatable articulated joint is designed as a ball joint.

14. The X-ray optics assembly according to claim 11, further comprising a first adjustment mechanism for pivoting the adjustment unit about a first axis (y) and a second adjustment mechanism for rotating the adjustment unit about a second axis (x).

15. The X-ray optics assembly according to claim 12, wherein the carriage is movable via guides between two end stops on a base body of the X-ray optics assembly.

16. The X-ray optics assembly according to claim 15, wherein a guide bolt is guided on or in the carriage, and is movable with respect to the carriage along a sliding direction (SRF), in parallel to a travel direction (VRS) of the carriage, and wherein in the sliding direction (SRF) a contact element is formed on or in the carriage, on both sides of the guide bolt, and is movable on or in the carriage in parallel to the sliding direction (SRF) and supported on the carriage via a respective first spring element.

17. The X-ray optics assembly according to claim 16, wherein a drive spindle, on which a spindle nut that is guided on the base body rests, is provided on the base body of the X-ray optics assembly, and wherein the guide bolt is coupled to the spindle nut.

18. The X-ray optics assembly according to claim 11, wherein the adjustment unit includes a retaining element and an adjustment element, and wherein the retaining element has a ball section, a first connecting section from the ball section to the monochromator, and a second connecting section from the ball section to the adjustment element.

19. The X-ray optics assembly according to claim 13, wherein the adjustment unit is provided with a ball section situated between two joint socket elements that are pretensioned with respect to one another by means of one or more second spring elements.

20. The X-ray optics assembly according to claim 13, wherein a guide arrangement having two mutually facing guide sections is provided, between which the adjustment unit is guided with contact, so that the adjustment unit is pivotable about a first axis (y) which extends through a midpoint (M) of the ball joint and is perpendicular to a guide plane (FEB) that is parallel to the guide sections, wherein the adjustment unit is rotatable about a second axis (x) which extends through the midpoint (M) of the ball joint and is perpendicular to the first axis (y), and wherein the adjustment unit rests against the guide sections at a distance from the midpoint (M) of the ball joint with respect to the direction of the second axis (x), so that pivoting of the adjustment unit about a third axis (z) which extends through the midpoint (M) of the ball joint and is perpendicular to the first axis (y) and the second axis (x) is blocked.

21. The X-ray optics assembly according to claim 20, wherein the guide arrangement is designed to be rotatable about the second axis (x), the adjustment unit resting against the guide sections at a distance from the midpoint (M) of the ball joint with respect to the direction of the third axis (z), so that when the adjustment unit rotates about the second axis (x), it also turns the guide arrangement.

22. The X-ray optics assembly according to claim 20, wherein the guide arrangement has a rotatably fixed design, the adjustment unit rests against the guide sections with circular cylinder lateral surface sections, and wherein a shared cylinder axis (ZA) of the circular cylinder lateral surface sections extends through the midpoint (M) of the ball joint, so that when the adjustment unit rotates about the second axis (x), the adjustment unit rotates about the shared cylinder axis (ZA) with respect to the guide arrangement.

23. The X-ray optics assembly according to claim 14, wherein the adjustment unit has an adjustment lever which protrudes essentially transversely with respect to the second axis (x), and on which the first and second adjustment mechanisms engage, and wherein the adjustment lever is deflectable via the first adjustment mechanism in a direction approximately parallel to the second axis (x), and is deflectable via the second adjustment mechanism in a direction approximately parallel to the first axis (y).

24. The X-ray optics assembly according to claim 14, wherein the first adjustment mechanism and the second adjustment mechanism each press the adjustment unit with the force of a respective third spring element against a displaceable adjustment stop.

* * * * *